United States Patent
Crowe

(10) Patent No.: US 10,940,275 B2
(45) Date of Patent: Mar. 9, 2021

(54) CANNABIS VAPORIZATION TEMPERATURE CONTROL

(71) Applicant: Vuber Technologies, LLC, Seattle, WA (US)

(72) Inventor: David Crowe, Lake Forest Park, WA (US)

(73) Assignee: Vuber Technologies, LLC, Seattle, WA (US)

( * ) Notice: Subject to any disclaimer, the term of this patent is extended or adjusted under 35 U.S.C. 154(b) by 104 days.

(21) Appl. No.: 16/009,408

(22) Filed: Jun. 15, 2018

(65) Prior Publication Data

US 2018/0361086 A1    Dec. 20, 2018

Related U.S. Application Data

(60) Provisional application No. 62/520,089, filed on Jun. 15, 2017.

(51) Int. Cl.
| | |
|---|---|
| H05B 3/00 | (2006.01) |
| A24F 47/00 | (2020.01) |
| A61M 15/06 | (2006.01) |
| A61M 11/04 | (2006.01) |
| H05B 1/02 | (2006.01) |

(52) U.S. Cl.
CPC .......... *A61M 11/042* (2014.02); *H05B 1/0288* (2013.01); *A61M 2205/3368* (2013.01); *A61M 2205/3653* (2013.01); *A61M 2205/50* (2013.01); *A61M 2205/8206* (2013.01)

(58) Field of Classification Search
CPC .......... A61M 15/0065–15/0071; A61M 15/06; A61M 15/008; A61M 15/0086–15/0088; A24F 47/002; A24F 47/008; H05B 3/0014; H05B 3/0019; H05B 3/78
See application file for complete search history.

(56) References Cited

U.S. PATENT DOCUMENTS

| | | | | |
|---|---|---|---|---|
| 2006/0047368 | A1* | 3/2006 | Maharajh | A24F 47/008 700/283 |
| 2014/0123990 | A1* | 5/2014 | Timmermans | A24F 47/008 131/328 |
| 2014/0345635 | A1* | 11/2014 | Rabinowitz | A24B 15/16 131/352 |
| 2017/0258142 | A1* | 9/2017 | Hatton | A24F 47/008 |
| 2018/0043114 | A1* | 2/2018 | Bowen | A61M 15/003 |
| 2018/0077967 | A1* | 3/2018 | Hatton | A61M 11/042 |

(Continued)

*Primary Examiner* — Michael A Laflame, Jr.
(74) *Attorney, Agent, or Firm* — Occhiuti & Rohlicek LLP

(57) ABSTRACT

It is an objective of the present invention to reduce the disadvantages in currently available Vaporizers by providing a method and system of controlling the output voltage of the Battery such that the electrical current within and the temperature of the heating element and Extract are controllable. The present invention discloses the Battery that operates by supplying voltage that varies with time and provides various automatically or manually selectable voltage-time profiles. The voltage is controlled by an integrated controller that is able to vary the battery output voltage via voltage modulation and is able to continuously vary the output voltage. The voltage is modulated using pulse width modulation. The integrated controller is capable of storing and executing an embedded program for voltage modulation.

20 Claims, 5 Drawing Sheets

(56) References Cited

U.S. PATENT DOCUMENTS

| | | | |
|---|---|---|---|
| 2018/0104214 A1* | 4/2018 | Raichman | A61P 25/36 |
| 2018/0317557 A1* | 11/2018 | Monsees | A61M 11/042 |
| 2019/0387796 A1* | 12/2019 | Cohen | A24F 47/008 |
| 2020/0022416 A1* | 1/2020 | Alarcon | B05B 11/00 |
| 2020/0046032 A1* | 2/2020 | Woodbine | H04L 67/12 |

* cited by examiner

CANNABIS VAPORIZATION TEMPERATURE CONTROL

CROSS-REFERENCE TO RELATED APPLICATIONS

This application claims priority to U.S. Provisional Application No. 62/520,089 filed on Jun. 15, 2017. The content of the above application is incorporated by reference in its entirety.

FIELD OF THE DISCLOSURE

The overall field of invention is devices and methods for controlled vaporization of liquids and solids.

BACKGROUND

Cannabis has long been used recreationally and medicinally, with smoking being the traditional and prevalent means for consumption. A variety of other means for consumption currently exist, while new consumption means are continually being developed.

Vaporization has gained prevalence as a means for consumption. Vaporization differs from smoking in that the cannabis or tobacco, extracts thereof, or cannabinoid concentrates are merely heated to the point of vaporization, rather than combusted. Vaporization ideally produces just inhalable vapor without smoke. Vaporization is a highly controllable process, whereby the amount of heating applied to either the plant or Extract can be precisely controlled, and the size of the resulting dose of medicament is much more predictable than the size of a dose taken through smoking. Vaporization differs from smoking in that the Plant or Extract is heated to a temperature high enough to volatilize the medicament into vapor but low enough to avoid combustion. Combustion products and byproducts, such as smoke and $NO_x$, may be undesirable for consumption for a variety of reasons, including health effects and flavor preference. Vaporization optimally produces no smoke and the vapor will exhibit a complete absence of any associated burnt flavor.

Optimal vaporization not only eliminates burnt flavor, but also preserves compounds that contribute to the overall flavor profile. Cannabis contains a wide variety of terpenes, each of which is associated with a distinct flavor, and together contribute to the cannabis flavor profile. Terpenes are the organic compounds responsible for much of the flavor profile of the Extract. Terpenes decompose at a rate that is directly related to temperature. When terpenes are exposed to high temperature, the terpenes decompose at a meaningful rate, and the result is a reduction in the complex natural flavor profile and can often result in a distinct and undesirable "burned" flavor. Therefore, it is desirable to control the temperature and time of heating of any plant or Extract being vaporized in order to optimize Vapor flavor and prevent undesirable decomposition of organic compounds.

Most Vaporizers operate through ohmic resistance heating, in which a battery portion of a Vaporizer supplies a voltage to a resistance heating element contained in an Atomizer in response to a command from the user. An Atomizer produces Vapor by heating Extract using ohmic resistance heating. In principal, a heating element is a resistance heater that will generate heat proportional to the voltage supplied by a battery. The temperature of the heating element will be a function of the output voltage of the battery, the resistance of the heating element, and the rate of heat dissipation due to radiation, conduction, convection, and phase change. Most available Vaporizers will heat extract to very high temperatures that result in rapid terpene degradation and a resulting poor or burned flavor. Ideal Extract vaporization will heat the Extract in a manner that minimizes terpene degradation. Terpene degradation can be reduced by limiting heating time and temperature.

Temperature feedback devices such as thermocouples and thermistors may be used for temperature feedback and control, but result in additional cost and complexity. Currently, most available Vaporizers suffer from uncontrolled heating of the heating element and extract. Because the Extract temperature is not controlled, temperatures rise such that terpenes may decompose and degrade at extremely high rates.

Additionally, Vaporizers are generally comprised of a battery portion, and an Atomizer portion. Batteries and Atomizers are each available from many distinct manufacturers with widely varying specifications such as output voltage, resistance, impedance, and other electrical properties. Batteries designed for Vaporizer use generally range in voltage output from 3V to 4V. Atomizers typically range in resistance from 1 Ω to 2.5 Ω The temperature/time curve of a given Atomizer-Battery combination will vary dramatically depending on the specifications of the component parts.

Furthermore, a known issue with many available batteries is that if used in combination with an Atomizer with less than 1 Ω resistance, the rate of discharge will be high enough that the battery can be damaged, and in some cases will lead to a catastrophic failure of the battery.

SUMMARY OF THE INVENTION

It is the object of the present invention to reduce the disadvantages in currently available Vaporizers by providing a method and system of controlling the output voltage of the Battery such that the electrical current within and the temperature of the heating element and Extract are controllable.

DEFINITIONS

Figure 1:
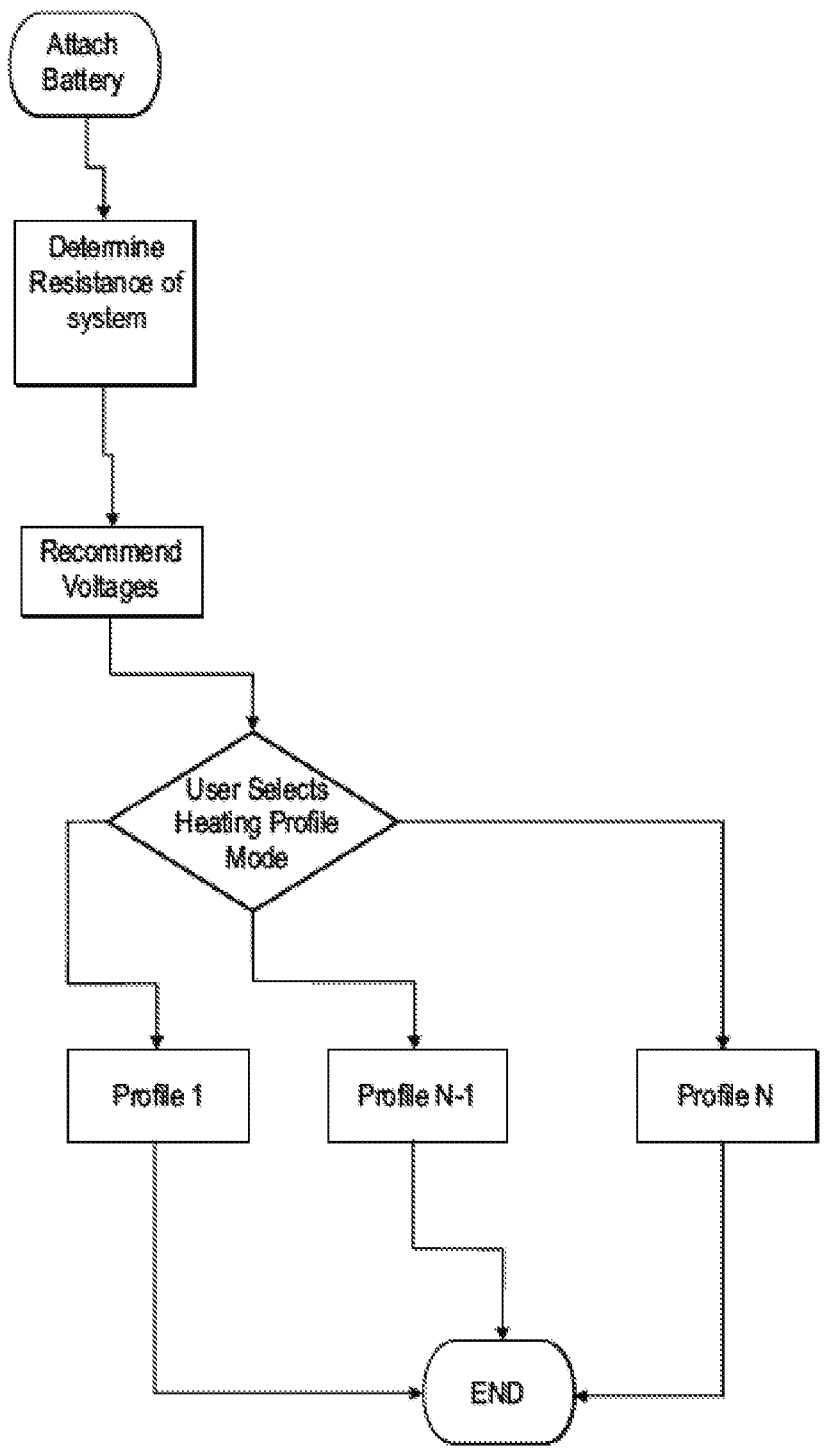
FIG. 1 Shows a flow diagram of the system preferred embodiment

Atomizer: an atomizer or cartomizer incorporating an ohmic resistance heater for use in vaporizing Extract.

Battery: A voltage source capable of outputting modulated voltage adapted for use with an Atomizer Vaporizer: A device comprising a Battery electrically coupled to an Atomizer Vapor: Gaseous or suspended liquid condensate Extract suitable for inhalation.

DETAILED DESCRIPTION

In the Summary above and in this Detailed Description, the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

The present invention is a Battery that operates by supplying voltage that varies with time and can provide various automatically or manually selectable voltage-time profiles. In the preferred embodiment Voltage is controlled by an integrated controller that is able to vary the battery output voltage via voltage modulation and is able to continuously vary said output voltage. In the preferred embodiment, voltage is modulated using pulse width modulation. The integrated controller would be capable of storing and executing an embedded program for voltage modulation.

FIG. 1 shows the general flow of operation of the preferred embodiment of the present invention. In this embodiment, the attached Atomizer's resistance properties are initially unknown. The Battery will measure or detect the resistance of an attached Atomizer upon attachment to the battery, and, when activated, the Battery will output a profiled voltage that depends on the resistance of the Atomizer.

In this embodiment, the Heating Profile Mode is selected automatically. The battery controller will measure or detect the resistance of the attached Atomizer and will recommend one of several stored voltage profiles based on the resistance.

In this embodiment, the resistance of the Atomizer is measured immediately after attachment to the battery. In other embodiments, the Battery may measure Atomizer resistance immediately before or after user activation.

In this embodiment, the profiled voltage will generally begin at a highest output voltage, and will be stepped down by 0.2V every three seconds for a total duration of 15 seconds. The highest output voltage will depend on the detected or measured Atomizer resistance.

Figure 2:
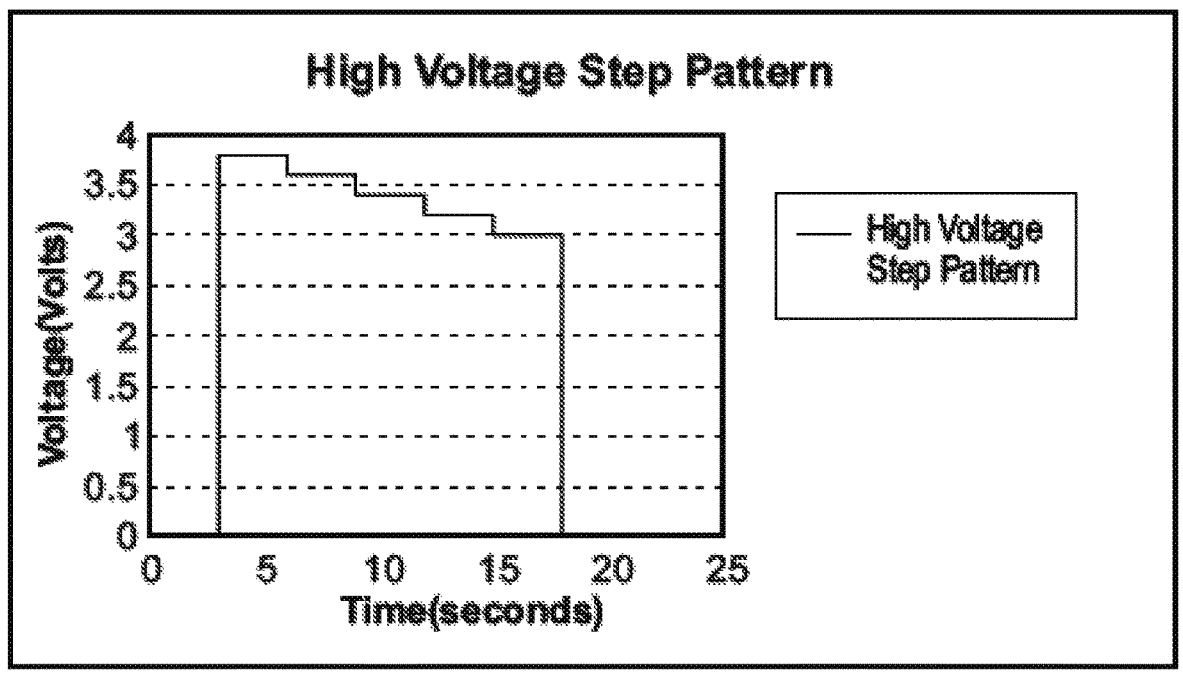
FIG. 2 Shows a diagram of a first profiled output voltage of the Battery

FIG. 2 shows the profiled voltage output of the preferred embodiment when the battery measures a resistance greater than 2.0 $\Omega$ in the attached Atomizer. The battery will output a first profiled output voltage pattern in which the highest output voltage is 3.8V. When activated by the user, the battery will output 3.8V for 3 seconds, then 3.6V for 3 seconds, then 3.4V for 3 seconds, then 3.2V for 3 seconds, then 3.0V for 3 seconds.

Figure 3:
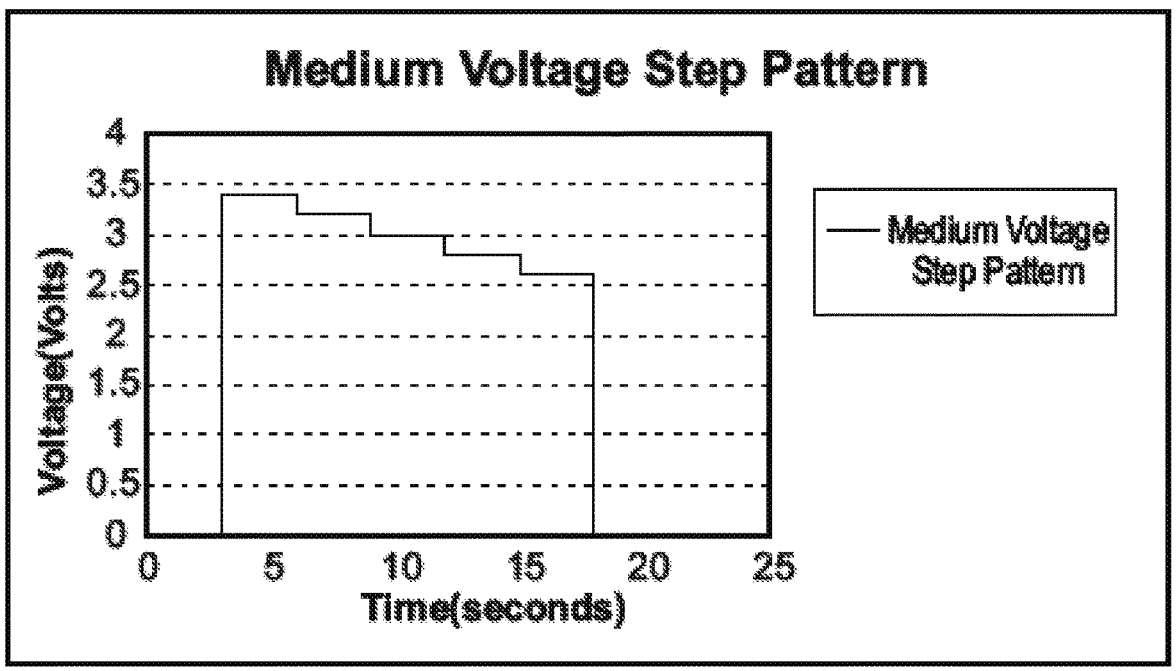
FIG. 3 Shows a diagram of a second profiled output voltage of the Battery

FIG. 3 shows the profiled voltage output of the preferred embodiment when the battery measures a resistance between 1.6 $\Omega$ and 2.0 $\Omega$ in the attached Atomizer. The battery will output a second profiled output voltage pattern in which the highest output voltage is 3.4V. When activated by the user, the battery will output 3.4V for 3 seconds, then 3.2V for 3 seconds, then 3.0V for 3 seconds, then 2.8V for 3 seconds, then 2.6V for 3 seconds.

Figure 4:
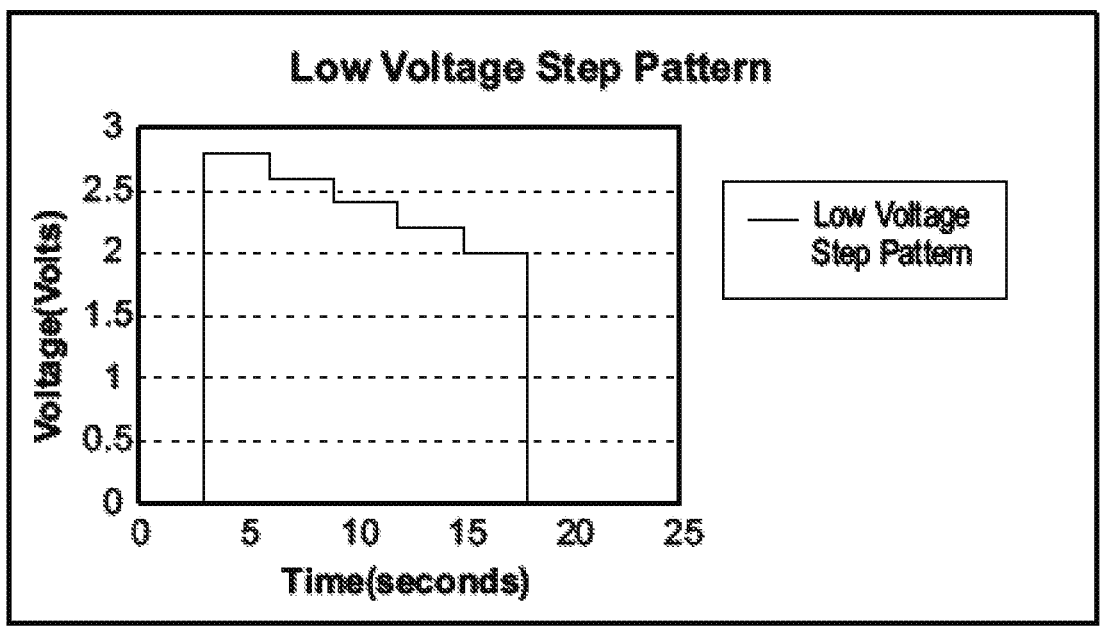
FIG. 4 Shows a diagram of a third profiled output voltage of the Battery

FIG. 4 shows the profiled voltage output of the preferred embodiment when the battery measures a resistance below 1.6 $\Omega$ in the attached Atomizer. The battery will output a third profiled output voltage pattern in which the highest output voltage is 2.8V. When activated by the user, the battery will output 2.8V for 3 seconds, then 2.6V for 3 seconds, then 2.4V for 3 seconds, then 2.2V for 3 seconds, then 2.0V for 3 seconds.

The preferred embodiment operates using stepped output voltage profiles. The stepped output voltage profiles are based on values that are permanently stored in the controller. Other embodiments may incorporate output voltage profiles that are calculated according to the measured Atomizer resistance and/or other variables. Voltage profiles may be smooth, stepped, continuous, discontinuous, or any combination thereof. Voltage output duration is 15 seconds in the preferred embodiment, but other embodiments may use longer or shorter durations. Output voltage profiles are generally chosen in order to produce a heating element temperature curve that will be effective in vaporizing Extract while minimizing terpene decomposition.

Figure 5:
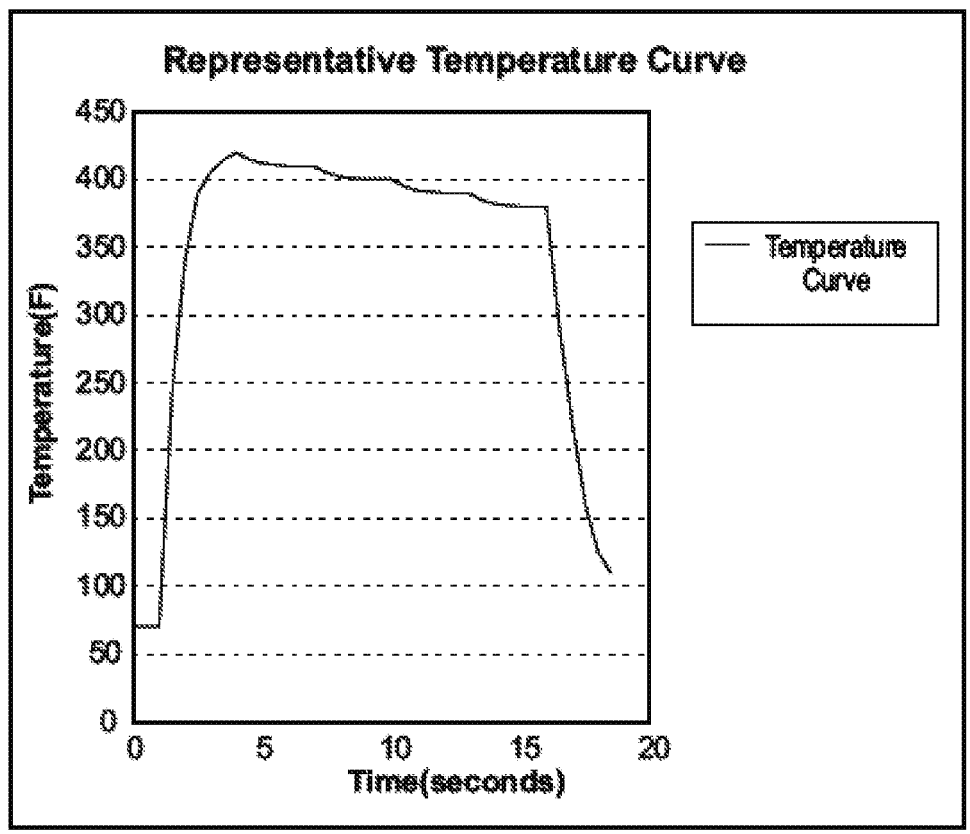
FIG. 5 Shows a representative temperature profile of an Atomizer heating element resulting from a profiled output voltage FIG. 6 Shows a flow diagram of a second embodiment of the system, and FIG. 7 Shows a block diagram of a temperature-controlling cannabis vaporization system.

FIG. 5 shows the Representative Temperature Curve that the stepped voltage profile will generate within an Atomizer. The temperature will climb to a maximum temperature and then it will gradually decrease over the duration of the operation. In this manner, terpene degradation is significantly reduced. In the preferred embodiment, the temperature will remain between 400F and 450F for a period of at least 10 seconds. As terpene degradation rate is a function of temperature, the internal temperature of the system should remain below 450F to limit terpene degradation. Alternative embodiments may heat to alternative temperature ranges to optimize for other factors, such as vaporization rate. In an embodiment, temperature is maintained between 500F and 550F for significantly increased vaporization rate. In an alternative embodiment, temperature is maintained between 450F and 500F to balance terpene degradation with vaporization rate.

Figure 6:
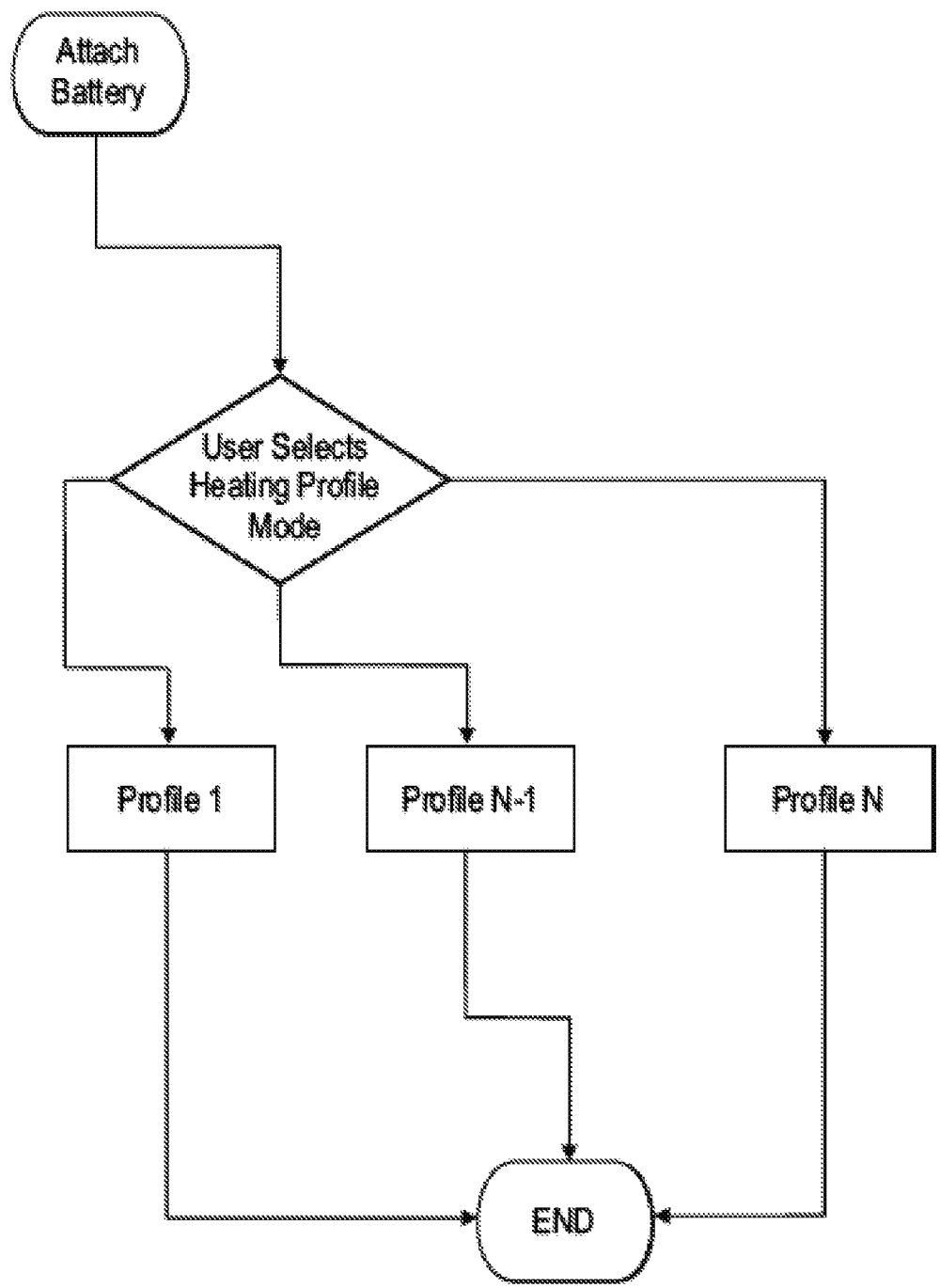
Figure 7:
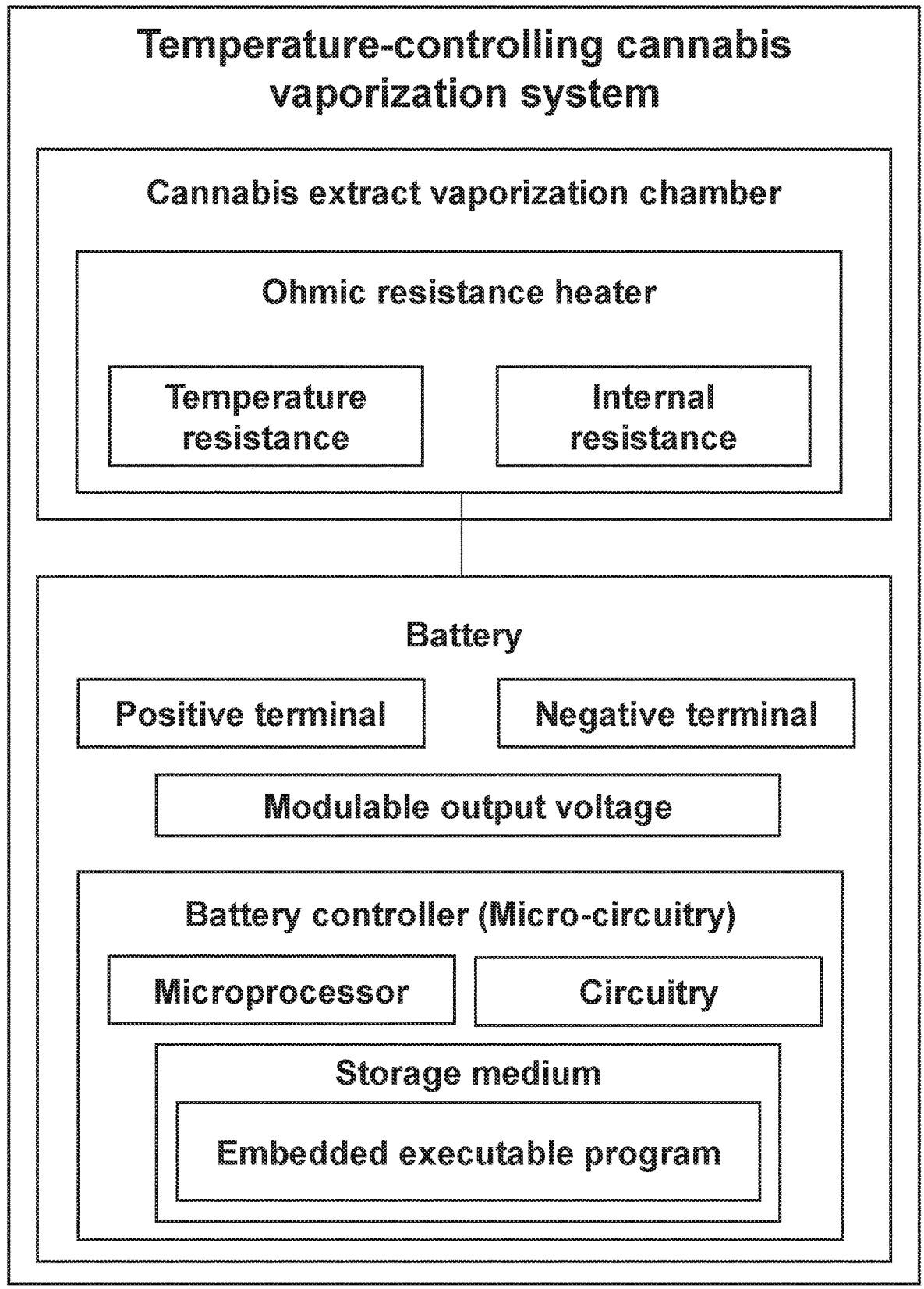

FIG. 6 shows the operation flow for another embodiment. In this embodiment, the Battery is paired with an Atomizer with known resistance properties. In this case, the user may select an output voltage profile by operation of a button on the device. In this embodiment, the user may select among output voltage profile modes by depressing the button in specific sequences. In this embodiment, the user may select from a constant or stepped voltage. Other stored or calculated voltage profiles may also be employed. FIG. 7 Shows a block diagram of a temperature-controlling cannabis vaporization system. The temperature-controlling cannabis vaporization system comprises a cannabis extract vaporization chamber adapted to house the ohmic resistance heater. The ohmic resistance heater includes a temperature and an internal resistance. The temperature-controlling cannabis vaporization system further comprises the battery having a positive terminal, a negative terminal, a modulable output voltage, and integrated micro-circuitry for controlling the modulable output voltage. The battery is connected to the resistance heater such that the resistance heater forms a circuit between the battery positive and negative terminals and supplies the modulable output voltage across the resistance heater such that the resistance heater temperature is modulable as a function of the output voltage. The integrated micro-circuitry executes an embedded program for output voltage control. The embedded program operates to cause the battery to output the modulable output voltage such that the voltage is modulated with time and the internal temperature will vary as a function of the voltage. The modulable voltage is modulated such that the resistance heater temperature is between 400 F and 550 F for a duration of at least 5 seconds. The modulable voltage may be modulated such that the resistance heater temperature is between 400 F and 450 F for a duration of at least 5 seconds. The modulable voltage may be modulated such that the resistance heater temperature is between 450 F and 500 F for a duration of at least 5 seconds. The modulable voltage may be modulated such that the resistance heater temperature is between 500 F and 550 F for a duration of at least 5 seconds. The modulable voltage is initially OV, then modulated to a maximum voltage, then reduced, such that the maximum voltage is reached within the first 4 seconds of execution of the embedded program. The embedded program may first detect the resistance of the circuit and modulate the output voltage according to the detected resistance. The modulable voltage varies such that the resistance heater temperature remains between 400 F and 450 F for a duration of at least 5 seconds. The modulable voltage varies such that the resistance heater temperature remains between 450 F and 500 F for a duration of at least 5 seconds. The modulable voltage varies such that the resistance heater temperature remains between 500 F and 550 F for a duration of at least 5 seconds. The modulable voltage varies such that the resistance heater temperature remains between 400 F and 450 F for a duration of at least 10 seconds. The modulable voltage is initially 0V, then modulated to a maximum voltage, then reduced, such that the maximum voltage is reached within the first 4 seconds of execution of the embedded program. The maximum voltage is between 2.5V and 4.0V.

Embodiments may employ any number of selectable output voltage profiles. Output voltage profile selection may be automatic in response to variables such as Atomizer resistance, stored inputs, state of charge, user inputs via user interface, or other sensed inputs. Alternatively, output voltage profile selection may be manually selected by the user via operation of the user interface. User interface may be a button, switch, touch sensitive pad or region, radio signal, electronic signal, or other means for interfacing with the battery.

Preferred Method of Use

In the preferred method of use, the Battery is coupled to an Atomizer such that the Battery is able to supply a voltage differential to an ohmic resistance heater circuit. The user will depress a button on the Battery that will signal to the controller to output a voltage that will vary over time in a predefined pattern or profile.

While preferred and alternate embodiments have been illustrated and described, as noted above, many changes can be made without departing from the spirit and scope of this CANNABIS VAPORIZATION TEMPERATURE CONTROL. Accordingly, the scope of the CANNABIS VAPORIZATION TEMPERATURE CONTROL is not limited by the disclosure of these preferred and alternate embodiments. Instead, the scope of the CANNABIS VAPORIZATION TEMPERATURE CONTROL is to be determined entirely by reference to the claims. Insofar as the description above and the accompanying drawings (if any) disclose any additional subject matter that is not within the scope of the claims below, the inventions are not dedicated to the public and Applicant hereby reserves the right to file one or more applications to claim such additional inventions.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example of a generic series of equivalent or similar features.

Any element in a claim that does not explicitly state "means for" performing a specified function, or "step for" performing a specific function is not to be interpreted as a "means" or "step" clause as specified in 35. U.S.C. § 112 ¶6. In particular, the use of "step of" in the claims herein is not intended to invoke the provisions of U.S.C. § 112 ¶16.

The invention claimed is:

1. A temperature-controlling cannabis vaporization system, comprising:
   a cannabis extract vaporization chamber adapted to house an ohmic resistance heater, wherein said ohmic resistance heater having a temperature and an internal resistance, and
   a battery having a positive terminal, a negative terminal, a modulable output voltage, and integrated micro-circuitry for control of said modulable output voltage,
   wherein said battery automatically measures or detects said resistance of said resistance heater based on a connection of said battery to said resistance heater such that said resistance heater forms a circuit between said battery positive and negative terminals, and
   wherein said battery selects a voltage profile from stored voltage profiles based on said measured or detected resistance and supplies said modulable output voltage of said selected voltage profile across said resistance heater, wherein said modulable output voltage is supplied in a step wise manner starting from a highest output voltage of said selected voltage profile that is stepped down to one or more lower output voltages of said selected voltage profile such that said resistance heater temperature is modulable as a function of said modulable output voltage, said integrated micro-circuitry executing an embedded program for output voltage control, wherein said embedded program operates to cause said battery to output said modulable output voltage such that said modulable output voltage is modulated with time in said step wise manner and said internal temperature varies as a function of said modulable output voltage, and wherein said modulable output voltage is modulated such that said resistance heater temperature is between 400 F and 550 F for a duration of at least 5 seconds.

2. The system of claim 1, wherein said modulable output voltage is modulated such that said resistance heater temperature is between 400 F and 450 F for a duration of at least 5 seconds.

3. The system of claim 1, wherein said modulable output voltage is modulated such that said resistance heater temperature is between 450 F and 500 F for a duration of at least 5 seconds.

4. The system of claim 1, wherein said modulable output voltage is modulated such that said resistance heater temperature is between 500 F and 550 F for a duration of at least 5 seconds.

5. The system of claim 1, wherein said modulable output voltage is initially 0V, then modulated to a maximum voltage, then reduced, such that said maximum voltage is reached within first 4 seconds of execution of said embedded program.

6. The system of claim 1, wherein said embedded program will first detect said resistance of said circuit and modulate said output voltage according to said detected resistance.

7. The system of claim 6, wherein said modulable output voltage varies such that said resistance heater temperature remains between 400 F and 450 F for a duration of at least 5 seconds.

8. The system of claim 6, wherein said modulable output voltage varies such that said resistance heater temperature remains between 500 F and 550 F for a duration of at least 5 seconds.

9. The system of claim 6, wherein said modulable output voltage varies such that said resistance heater temperature remains between 400 F and 450 F for a duration of at least 10 seconds.

10. The system of claim 9, wherein said modulable output voltage is initially 0V, then modulated to a maximum voltage, then reduced, such that said maximum voltage is reached within first 4 seconds of execution of said embedded program.

11. The system of claim 10, wherein said maximum voltage is between 2.5V and 4.0V.

12. A vaporizer, comprising:
a battery capable of supplying a voltage,
a battery controller capable of a variable modulation of said voltage to produce a variable output voltage,
said battery controller being micro-circuitry comprising:
a microprocessor in conjunction with a tangible storage medium,
an embedded executable program stored in said tangible storage medium and executed by said microprocessor, and
circuitry adapted for pulse width modulation of said voltage, wherein said executable program being adapted for an algorithmic determination of a recommended variable output voltage sequence, wherein said recommended variable output voltage sequence is determined based on a selection of a voltage profile from stored voltage profiles, wherein said voltage profile is selected based on a resistance of an ohmic resistance heater atomizer having a temperature, wherein said recommended variable output voltage sequence being is supplied to said ohmic resistance heater atomizer, wherein said temperature is a function of said recommended variable supply voltage sequence, and wherein said recommended variable supply voltage sequence being adapted to maintain said internal temperature between 400 F and 450 F for a period of at least 5 seconds.

13. The vaporizer of claim 12, wherein said recommended variable supply voltage sequence is recommended by determination of ohmic resistance heater resistance properties of said resistance.

14. The vaporizer of claim 13, wherein said internal temperature is maintained between 400 F and 450 F for a period of at least 10 seconds.

15. The vaporizer of claim 13, wherein said internal temperature is maintained between 400 F and 450 F for a period of at least 15 seconds.

16. A method for vaporization temperature control, comprising:
connecting a battery having a modulable output voltage to an ohmic resistance heater having a temperature and housed within an atomization chamber to form a circuit,
determining a resistance of said circuit,
placing a dose of cannabinoid extract in thermal contact with said ohmic resistance heater,
algorithmically determining a recommended voltage sequence based on said resistance of said circuit, wherein said recommended voltage sequence is determined based on a selection of a voltage profile from stored voltage profiles, wherein said voltage profile is selected based on said resistance,
outputting said recommended voltage sequence by modulating said modulable output voltage, wherein said modulable output voltage is supplied in a step wise manner starting from a highest output voltage of said selected voltage profile that is stepped down to one or more lower output voltages of said selected voltage profile,
raising said temperature to between 400 F and 450 F in accordance with said modulable output voltage, and
maintaining said temperature between 400 F an 450 F for at least 5 seconds.

17. The vaporizer of claim 16, wherein said modulable output voltage is modulated via pulse width modulation.

18. The vaporizer of claim 17, wherein said temperature is maintained between 400 F and 450 F for at least 10 seconds.

19. The system of claim 6, wherein said modulable voltage varies such that said resistance heater temperature remains between 450 F and 500 F for a duration of at least 5 seconds.

20. The system of claim 1, wherein said voltage profile is selected from said stored voltage profiles to produce a heating element temperature curve that is effective in vaporizing extract while minimizing terpene decomposition.

* * * * *